United States Patent [19]
Adams

[11] Patent Number: 5,425,749
[45] Date of Patent: Jun. 20, 1995

[54] PREEMPTIVE CARDIOVERSION THERAPY IN AN IMPLANTABLE CARDIOVERTER DEFIBRILLATOR

[75] Inventor: Theodore P. Adams, Edina, Minn.

[73] Assignee: Angeion Corporation, Minneapolis, Minn.

[21] Appl. No.: 122,894

[22] Filed: Sep. 16, 1993

[51] Int. Cl.⁶ .............................................. A61N 1/39
[52] U.S. Cl. .................................................. 607/5
[58] Field of Search ......................................... 607/4–8

[56] References Cited

U.S. PATENT DOCUMENTS

| | | | |
|---|---|---|---|
| 4,375,817 | 3/1983 | Engle et al. | 607/4 |
| 5,014,697 | 5/1991 | Pless et al. | 607/7 |
| 5,063,928 | 11/1991 | Grevis et al. | 607/7 |
| 5,201,321 | 4/1993 | Fulton | 607/5 |

OTHER PUBLICATIONS

Kroll et al., Slope Filtered Pointwise Correlation Dimension Algorithm and Its Evaluation With Prefibrilation Heart Rate, Journal of Electrocardiology vol. 24, Supplement, pp. 97–101.

Primary Examiner—William E. Kamm
Attorney, Agent, or Firm—Joel D. Skinner, Jr.

[57] ABSTRACT

A method for use with an implantable cardioverter defibrillator apparatus of the type having a microprocessor-based control circuit, a charging circuit communicatively connected to the control circuit, a small charge storage capacitor, a large charge storage capacitor, switches, and charge output terminals, of delivering a preemptory shock to a patient, comprising the steps of a.) receiving physiological information pertaining to the onset of a deleterious cardiac event; b.) charging the small charge storage capacitor in the implantable cardioverter defibrillator apparatus immediately after step (a); c.) reviewing the information to confirm the onset of a cardiac event; and d.) delivering a preemptory charge from the small charge storage capacitor to the patient if the onset of a cardiac event is confirmed. An apparatus for practicing the above method is also discussed.

8 Claims, 2 Drawing Sheets

PREEMPTIVE CARDIOVERSION THERAPY IN AN IMPLANTABLE CARDIOVERTER DEFIBRILLATOR

BACKGROUND OF THE INVENTION

1. Technical Field

This invention relates to medical diagnostic and therapeutic apparatus and methods, and more particularly to an implantable cardioverter defibrillator method and apparatus for delivering a preemptory cardioversion or defibrillation pulse to a patient upon detection of predetermined physiological information related to cardiac function. The method and apparatus of this invention provide a means of delivering cardioverter defibrillator therapy to a patient having an implantable cardioverter defibrillator as soon as possible after the onset of a cardiac event such as arrhythmia (for example ventricular tachycardia or ventricular fibrillation) increase the chances of patient survival from such an event.

2. Background Information

The implantable cardioverter defibrillator (ICD) is a well recognized and important tool for managing the health of patients who have a history of heart problems, for example in the control of arrhythmias. Cardioversion involves the administration of a low energy shock (typically 0.1–5 joules (J)), via implanted electrodes, converts the arrhythmic heart rate. The ICD is further capable of resuscitating patients who experience cardiac arrest, via defibrillation. Defibrillation of the heart is accomplished by applying a high energy electrical waveform to cause the cessation of rapid uncoordinated contractions of the heart (fibrillation) and restoring the normal beating of the heart.

Referring to FIG. 1, currently, the process of converting a suspected arrhythmia or fibrillation to a normal heart rhythm, via an implantable cardioverter defibrillator (ICD), involves the following steps:

1. Detection— Detecting, during a time period 12, either a fibrillation 10 or another high rate arrhythmia. Detection may be accomplished by detecting a heart rate above a predetermined threshold value for a specified number or count of heart beats or by another or an additional algorithm that looks at waveform morphology, rate acceleration, rate stability or other criteria.

2. Charging— If cardioversion or defibrillation (vis-á-vis antitachy pacing) is warranted, charge storage means, typically capacitors, are charged during time period 13. The charging process can take from one to fifteen seconds depending upon the selected energy level and the state of the batteries.

3. Confirmation— After charging the capacitors, non-committed type devices reexamine ("take a second look at") the heart rate and discharge the capacitor internally if the heart rate has deceased spontaneously. If the rate still exceeds the threshold for a specified number of intervals, the charge is held. In committed devices, this step is omitted.

4. Shock— The energy stored in the capacitor is delivered 14 to the heart via implanted electrodes.

The above-referenced process, from detection of arrhythmia (including fibrillation) to capacitor charge up, takes between 5 to 25 seconds to complete. In the meantime, the patient may be fibrillating for 10 to 25 seconds before a defibrillation shock is applied. However, it is well established in the literature that there is a direct relationship between the elapsed time from onset of fibrillation to defibrillation and the minimum energy required therefor, the defibrillation threshold. Thus, it is in the best interest of the patient to receive therapy as soon as possible after onset of the arrhythmia, especially if the arrhythmia is fibrillation.

The typical ICD utilizes a rather large capacitor or assemblage of capacitors to store charge and to discharge a shock or pulse to the patient. It is known that a given energy delivered in the form of high currents (or voltages) for shorter durations are more effective than lower currents delivered for longer duration's. It is further known that a small value capacitor takes less time to charge to a given voltage than a large value capacitor and that a small value capacitor can deliver a given amount of energy in a shorter period time than a large value capacitor.

In summary, various implantable cardioverter/defibrillator devices and/or methods have been used or proposed in the past to defibrillate or otherwise control the activity of the human heart. However, these implantable cardioverter/defibrillator devices and methods have significant limitations and shortcomings, foremost of which is the time delay from detection of a cardiac event to capacitor charge-up and discharge.

Despite the need in the art for an implantable cardioverter/defibrillator apparatus and method which overcome the shortcomings and limitations of the prior art, none insofar as is known has been developed or proposed. Accordingly, it is an object of the present invention to provide an implantable cardioverter/defibrillator method and device which is capable of delivering a shock in the shortest time possible, to thereby defibrillate successfully more often and to utilize less energy in the process. A further object of this invention is to provide an apparatus and method which utilizes a relatively small charge storage mechanism which is able to deliver a preemptory shock at an early stage in a cardiac event. Another object of this invention is to provide an apparatus and method which anticipates the onset of fibrillation or other arrhythmia and charges a preemptory shock capacitor before the fibrillation or other arrhythmia is actually detected to thereby deliver a cardioverting shock immediately upon detection or confirmation of the presence of such fibrillation or other arrhythmia. It is a further object of this invention to provide a method and apparatus which is reliable, safe, compact (in the case of the apparatus) and which otherwise overcome the limitations and shortcomings of the prior art.

SUMMARY OF THE INVENTION

The method of the present invention is for use with an implantable cardioverter defibrillator to deliver therapy as soon as possible after the onset of a cardiac event such as arrhythmia, including fibrillation, to increase the chances of patient survival from such an event. The apparatus of the present invention provides a means of carrying out the method of delivering cardioverter defibrillator therapy at an early stage.

The method of the invention is for delivering a preemptory shock to a patient and, in its most basic form, comprises the steps of:

a.) receiving physiological information pertaining to the onset of a deleterious cardiac event;

b.) charging the small charge storage capacitor in the implantable cardioverter defibrillator apparatus immediately after step (a);

c.) reviewing the information to confirm the onset of a cardiac event; and d.) delivering a preemptory charge from the small charge storage capacitor to the patient.

The apparatus of the invention implements the above referenced invention and, in its most basic form, comprises:

a.) control means;

b.) a charging circuit communicatively connected to the control means;

c.) small charge storage means connected to the charging circuit, the small charge storage means being charged immediately upon detection of information pertaining to the onset of a deleterious cardiac event;

d.) large charge storage means connected to the charging circuit;

e.) switch means connected to the small and large charge storage means; and f.) charge output means connected to the switch means for electrical communication with the heart of a patient.

The benefits of this invention will become clear from the following description by reference to the drawings.

DESCRIPTION OF THE PREFERRED EMBODIMENT

Figure 2:
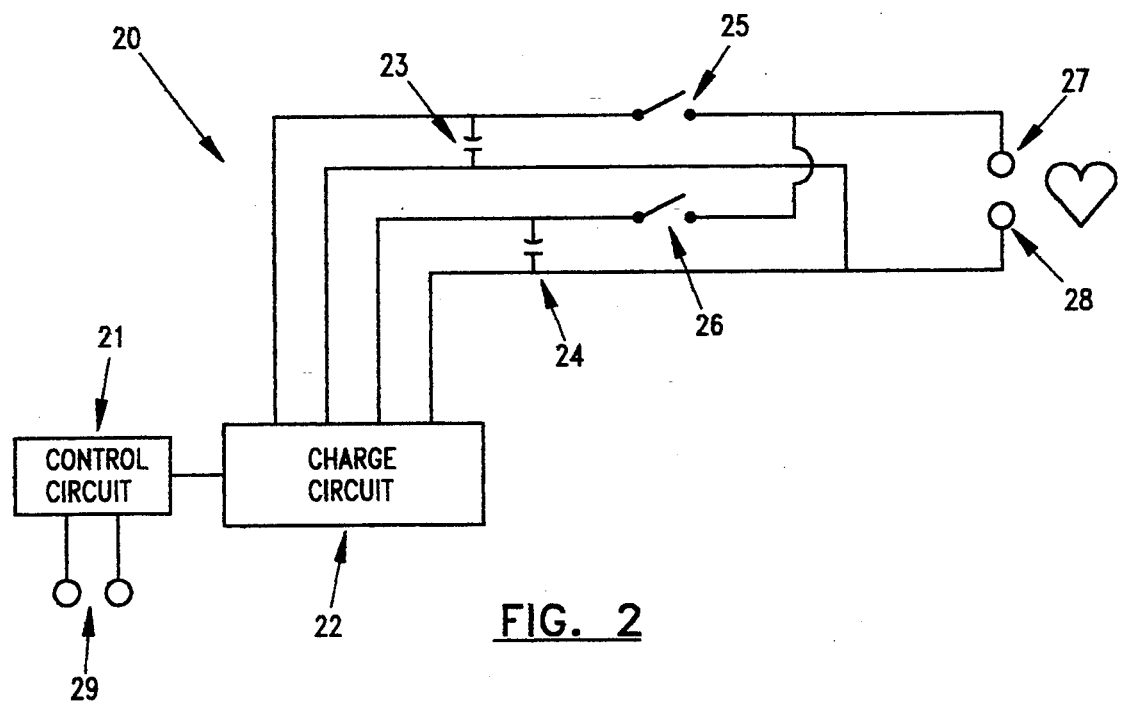
FIG. 2 is a schematic circuit diagram of the apparatus of the present invention.

Referring to FIG. 2, the implantable cardioverter defibrillator apparatus 20 of the present invention basically comprises a control circuit 21, preferably microprocessor based, a charge circuit 22, a relatively large capacitor 23 of 50–100 microfarads ($\mu F$), preferably 90 $\mu F$, and a smaller capacitor 24 of 10–50 $\mu F$, preferably 15 $\mu F$. The large capacitor 23 stores 0–30 joules(J) of energy, preferably 5.6 J and a small capacitor 24 stores 0.1–5 J, preferably 1.5 J. A pair of switches 25 and 26 are connected between electrode terminals 27 and 28 and the capacitors 23 and 24, respectively. The larger capacitor 24 is used in a conventional manner to deliver high energy defibrillation or small cardioversion pulses. The smaller capacitor 24 is utilized to provide a preemptory shock as will be described further below. The charge circuit 22 includes battery means and is utilized to charge the capacitors 23 and 24 when directed to do so by the control circuit 21. The control circuit 21 has input means 29 to receive physiological information related to cardiac function.

Figure 1:
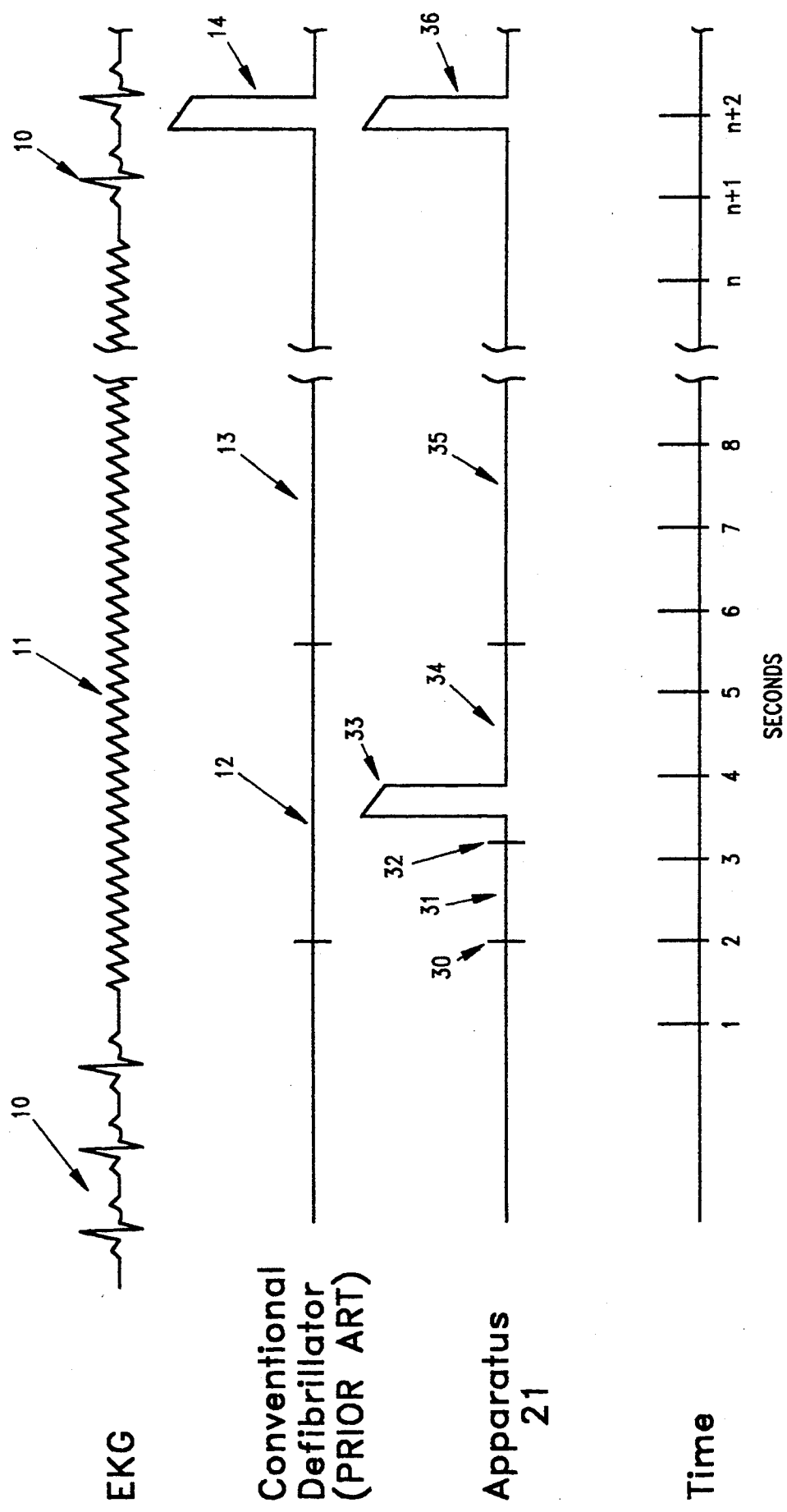
FIG. 1 is a composite graph showing the sequence and timing of steps taken by a typical prior art implantable cardioverter defibrillator and by the apparatus and method of the present invention.

The method of the present invention involves a multi-step process which is implemented by program instructions in the microprocessor based control circuitry 21 of the implantable cardioverter defibrillator 20. The method enables the provision of cardioverter defibrillator therapy in patients having and implantable cardioverter defibrillator as soon as possible after onset of a predetermined cardiac event. Referring again to FIG. 1, in the first step 30 of the method, the ICD either detects or predicts the onset of an arrhythmia, possibly a fibrillation. Such detection may be made by first detecting the presence of a burst of "n" number of high rate heartbeats, this being indicative of a potential arrhythmia. The rate of such beats is approximately 200 beats per minute. The number of such beats is approximately 3. This initial alert signals the microprocess 21 and the device 20 begins to process incoming data by a conventional algorithm.

An alternative method for the initial phase of the process of this invention involves predicting or anticipating the occurrence of fibrillation as is described in *Slope Filtered Pointwise Correlation Dimension Algorithm and Evaluation with Prefibrillation Heart Rate Data*, by M. W. Kroll and K. W. Fulton. This method involves the use of a heart rate variability algorithm to anticipate the onset of fibrillation. Although this method is preferred, still other methods exist for detecting or predicting the onset of fibrillation, for example one based on waveform morphology, rate acceleration, or rate stability and they too may be utilized in this initial phase, consistent with the overall teachings of this invention.

The Slope Filtered Pointwise Correlation Dimension Algorithm is used to predict eminent fibrillation and involves the following process:

1. Fix point for correlation dimension calculation.
   A. Set embedding dimension (e) to 2, r to 0.
      i) Increase r to include the first 10 neighbors.
      ii) Calculate the slope of log N versus log r for these 10 points ($=d'$). Continue "plotting" log N versus log r until N=1,000.
      iii) Find longest length of plot with <30% wiggle from $d'$ value.
      iv) Set $d_3$=the slope of this length of the plot.
   B. Increment e (embedding dimension).
2. Calculate "saturation deviation"=std. dev. $\{d_9, d_{10}, d_{11}, d_{12}\}$.
3. If saturation deviation <0.4 accept point.
4. Analyze next point.

In the above-referenced pseudocode for each point in a data set,

N=the number of neighbors for a point;

r=radius;

d=lim log N/log r, as r approaches 0; and

"wiggle" is the maximum change in $\delta \log N/\delta \log r$ (the "slope") as r increase.

The slope filtered pointwise correlation dimension algorithm calculates a correlation dimension for each point in a data set. It begins by fixing a point to use as an origin. Saturation deviation is the measure of the convergence of the dimension estimates as the embedding dimension increase. The algorithm finds the longest length of stable slope and calls that the dimension ($d_e$) for that embedding dimension e. The standard deviation of the last four $d_e$s (referred to as the saturation deviation) must be less than 0.4 for the point to be accepted to provide a trustworthy estimate of the correlation dimension.

It is the interaction of the wiggle factor and the saturation deviation that leads to the acceptance of a given origin point for an independent estimate of the correlation dimension. The slopes are used to filter the pointwise correlation dimension estimate.

The slope filtered pointwise correlation dimension gives a result at most points and is accurate at those points. The algorithm has been validated on mathematical data with known correlation dimensions. The algorithm has also been utilized in animal and clinical studies wherein it was found that the pointwise correlation dimension of heart rate data, as calculated by the slope filtered algorithm, appears to predict fibrillation in ischemic animals and in human arrhythmia patients. This process is used in the initial phase 30 of the present invention to anticipate arrhythmia or fibrillation before its actual onset to allow capacitor charge up to take place at an early stage as is described below.

Upon receiving the initial alert 30, the small capacitor 24 is immediately charged 31. This step 31 takes approximately 1-2 seconds. Alternately, the small capacitor may be a low leakage device which is continuously charged. At the conclusion of the small capacitor charging phase 31, the small capacitor is discharged during interval 33 across the heart providing the peremptory shock. Alternatively an additional step 32 in the method is to reevaluate the detection or anticipation made in the initial phase 30, and if reconfirmed, then discharge the small capacitor 24 during interval 33 across the heart to provide the preemptory shock 36.

If the initial phase 30 involves the detection of high rate beats, a second look at the succeeding heartbeat interval is taken, and confirmation is made if the interval is still short. If anticipation was made by the Slope Filtered Pointwise Correlation Dimension Algorithm, confirmation may be made by noting a sustained high rate, for example. The total elapsed time from the first fast beat to the initial or preemptory shock is on the order of 2-3 seconds but importantly is less than 3 seconds. The term "preemptory" as used herein to describe the initial pulse or shock refers to that pulse which is delivered first after arrhythmia onset and wherein normally applied detection criteria for confirming and diagnosing heart rhythm is bypassed.

If the heart arrhythmia is successfully converted, the large capacitor 23 is not charged. If the arrhythmia is not converted, conventional detection 34 continues along with charging 35 of the large capacitor 23. The cardioverting or defibrillating pulse 36 may then be delivered.

Utilizing the circuitry 20 disclosed above, wherein the small capacitor 24 is 20 μF and the large capacitor 23 is 90 μF, and assuming they are both charged to the same voltage, approximately 750 volts(V), approximately 5.6 joules (J) of energy is expended utilizing the method of this invention. In contrast, a typical ICD utilizes approximately 25 J energy. Thus, approximately 2/9ths of the energy normally required is used by practicing this method. Moreover,the small capacitor 24 is typically charged to an even lower voltage, approximately 380 V, or at a 1.5 J energy level. This results in a clear energy savings.

Although the preferred apparatus embodiment for practicing the method of this invention comprises separate and distinct large and small capacitors, it is within the purview of the invention to utilize a single large capacitor to discharge both the large and small shocks since charge time is proportional to stored energy regardless of the value of the capacitor.

Another advantage of this method is that the low value capacitor utilized also presents lower leakage currents than does a large capacitor. This is particularly important where the small capacitor is kept continuously charged. Also, where an anticipatory method is utilized in the initial phase, the lower charging current allows the device 20 to have a longer anticipatory period in the initial phase. And finally, with respect to the anticipatory initial phase,the low charging currents would allow pre-charging of the smaller capacitor to further increase the effectiveness of the preemptory pulse by allowing it's shock to be delivered still sooner after the start of an arrhythmia.

Figure 3:
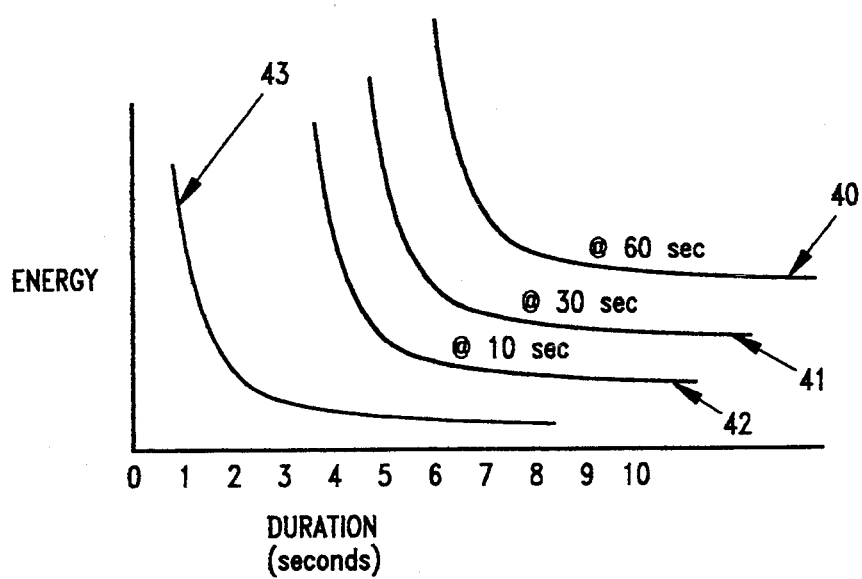
FIG. 3 is a graph showing a comparison of defibrillation Strength-Duration (S-D) curves with a cardioversion S-D curve.

The small capacitor 24 shock pulse width is delivered with a pulse width of about two milliseconds. This coincides with the ideal pulse width for cardioversion. Thus, a pulse delivered from the small capacitor 24 soon after the onset of arrhythmia would have a higher probability of cardioversion success with a lower probability of acceleration of the rhythm to fibrillation than conventional cardioversion pulses. Such a pulse may also be more effective for defibrillation than a conventional high energy pulse delivered later in the episode. FIG. 3 shows a comparison of defibrillation S-D curves 40, 41, and 42 with a cardioversion S-D curve 43. No data exists for defibrillation S-D curves for duration's less than approximately 10 seconds. It is, however, expected that additional S-D curves for defibrillation lie between the cardioversion S-D curve 43 and the 10 second defibrillation S-D curve 42.

As many changes are possible to the embodiments of this invention utilizing the teachings thereof, the descriptions above and the accompanying drawings should be interpreted in the illustrative and not the limited sense.

That which is claimed is:

1. A method of delivering a preemptory cardioverting shock to a patient for use with an implantable cardioverter defibrillator apparatus having control means, a charging circuit communicatively connected to said control means, means to store and discharge a first charge connected to said charging circuit, means, connected to said charging circuit and separate from said means to store and discharge a first charge, to store and discharge a second charge, switch means connected to each of said means to store and discharge, and charge output means connected to said switch means, comprising the steps of:
   a.) receiving physiological information pertaining to the onset of a deleterious cardiac event via said control means;
   b.) delivering a first charge of less than or equal to 5 J from said means to store and discharge a first charge to the patient's heart, for cardioverting the heart, via said switch means and said charge output means;
   c.) determining, via said control means, whether said first charge is effective at cardioverting the deleterious cardiac event;
   d.) charging said means to store and discharge a second charge of greater than or equal to 5 J via said control means and said charging circuit, if said first charge is not effective at rectifying the deleterious cardiac event; and
   e.) delivering said second charge from said means to store and discharge a second charge via said switch means and said charge output means, for defibrillating the patient's heart.

2. The method of claim 1, further comprising an initial step of continuously charging said means to store and discharge a first charge at 0.1-5 J, via said charging circuit.

3. The method of claim 1, further comprising a step of charging said small charge storage means, via said control means and said charging circuit, immediately after step (a).

4. The method of claim 1, wherein said means to store and discharge a first charge is a single capacitor having a value of 10-50 μF, charged to approximately 380 V and storing 0.1–5 J, and wherein said means to store and discharge a second charge is a single capacitor having a value of 50–100 μF charging to approximately 750 V and storing 5–30 J.

5. The method of claim 1, wherein said step of receiving physiological information predicts imminent fibrillation utilizing a slop filtered pointwise correlation dimension algorithm.

6. A method, for use with an implantable cardioverter defibrillator apparatus having control means, a charging circuit communicatively connected to said control means, small charge storage means connected to said charging circuit, a separate and distinct large charge storage means connected to said charging circuit, switch means connected to said small and large charge storage means, and charge output means connected to said switch means, of delivering a preemptory shock to a patient, comprising the steps of:
  a.) continuously charging said small charge storage means via said charging circuit;
  b.) receiving physiological information pertaining to the onset of a deleterious cardiac event via said control means;
  c.) delivering a preemptory charge of approximately 1.5 J from said small charge storage means to the patient, via said switch means and said charge output means, to cardiovert the patient's heart;
  d.) determining, via said control means, whether said preemptory charge is effective at cardioverting the patient's heart;
  e.) charging said large charge storage means via said control means and said charging circuit, if said preemptory charge is not effective at cardioverting the patient's heart; and
  f.) delivering a second charge of approximately 5.6 J from said large charge storage means to the patient via said switch means and said charge output means.

7. The method of claim 6, wherein said small charge storage means has a value of approximately 10–50 μF, charges to approximately 380 V and stores approximately 1.5 J, and wherein said large charge storage means has a value of approximately 50–100 μF, charges to approximately 750 V and stores approximately 5.6 J.

8. An implantable cardioverter defibrillator apparatus for delivering a preemptory shock to a patient, comprising:
  a.) control means for receiving physiological information from the patient pertaining to the onset of a deleterious cardiac event;
  b.) a charging circuit communicatively connected to said control means;
  c.) small charge storage means connected to said charging circuit, said small charge storage means discharging a small preemptory cardioverting shock of less than or equal to 5 J immediately upon detection of information pertaining to the onset of a deleterious cardiac event;
  d.) large charge storage means connected to said charging circuit, said large charge storage means being separate and distinct from said small charge storage means, said large charge storage means being charged and discharging a large defibrillating shock of greater than or equal to 5 J if said small shock is not effective at cardioverting the deleterious cardiac event;
  e.) switch means connected to and operative on said small and large charge storage means to deliver said small and large shocks;
  f.) charge output means connected to said switch means for electrical communication with the heart of a patient to deliver said small and large shocks.

* * * * *